United States Patent
Ewerlin

(10) Patent No.: US 7,647,826 B2
(45) Date of Patent: Jan. 19, 2010

(54) METHOD AND DEVICE FOR MEASURING OPERATIONAL DENSITY AND/OR OPERATIONAL SOUND VELOCITY IN A GASEOUS MEDIUM

(75) Inventor: Ulrich Ewerlin, Bochum (DE)

(73) Assignee: Elster GmbH, Mainz-Kastel (DE)

( * ) Notice: Subject to any disclaimer, the term of this patent is extended or adjusted under 35 U.S.C. 154(b) by 302 days.

(21) Appl. No.: 11/726,221

(22) Filed: Mar. 21, 2007

(65) Prior Publication Data

US 2007/0220976 A1 Sep. 27, 2007

(30) Foreign Application Priority Data

Mar. 22, 2006 (DE) .................... 10 2006 013 809

(51) Int. Cl.
*G01H 13/00* (2006.01)
(52) U.S. Cl. ...................................... 73/579
(58) Field of Classification Search .......... 73/579, 73/662, 597, 24.05, 24.01, 23.39; 367/172
See application file for complete search history.

(56) References Cited

U.S. PATENT DOCUMENTS

| | | | |
|---|---|---|---|
| 4,435,986 A | 3/1984 | Choffat | 73/702 |
| 4,803,671 A | 2/1989 | Rochling et al. | 367/166 |
| 4,991,153 A | 2/1991 | Tsuruoka et al. | 367/172 |
| 7,146,857 B2 * | 12/2006 | Hok | 73/579 |
| 2007/0193350 A1 * | 8/2007 | Nishizu et al. | 73/149 |

FOREIGN PATENT DOCUMENTS

| | | |
|---|---|---|
| DE | 3741558 A1 | 7/1988 |
| FR | 2 493 984 | 5/1982 |

OTHER PUBLICATIONS

Gillis et al., "Theory of the Greenspan viscometer," *Journal of the Acoustical Society of America*, vol. 114, No. 1, Jul. 2003, pp. 166-173. XP 012003533 (European SR).

* cited by examiner

*Primary Examiner*—Hezron Williams
*Assistant Examiner*—Tamiko D Bellamy
(74) *Attorney, Agent, or Firm*—Collard & Roe, P.C.

(57) ABSTRACT

A method for measuring operational density and/or operational sound velocity in a gaseous medium uses a sound transducer that is capable of vibrating, which is disposed in a housing in such a manner that chambers having the same volume are formed on both sides of the sound transducer, which are filled by the gaseous medium. The chambers are connected with one another by way of an open channel having defined dimensions. Using an exciter vibration applied to the sound transducer, the impedance of the sound transducer, which is influenced by the density of the gaseous medium, is determined within a frequency range that can be established, as a function of the exciter frequency. From this, the operational density and/or the operational sound velocity of the gaseous medium are determined using a plurality of characteristic frequencies of the sound transducer vibrating in the gaseous medium.

35 Claims, 6 Drawing Sheets

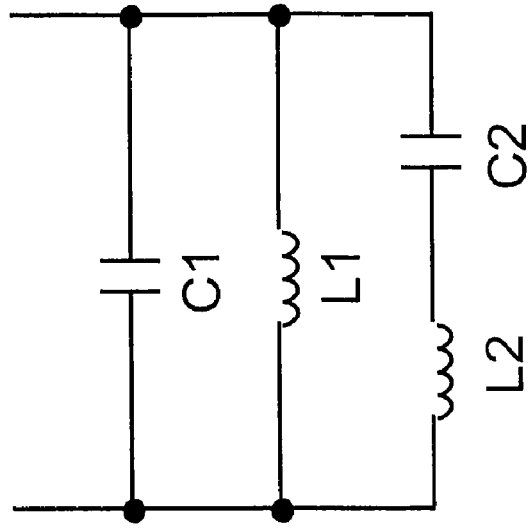
Fig. 2
Fig. 3
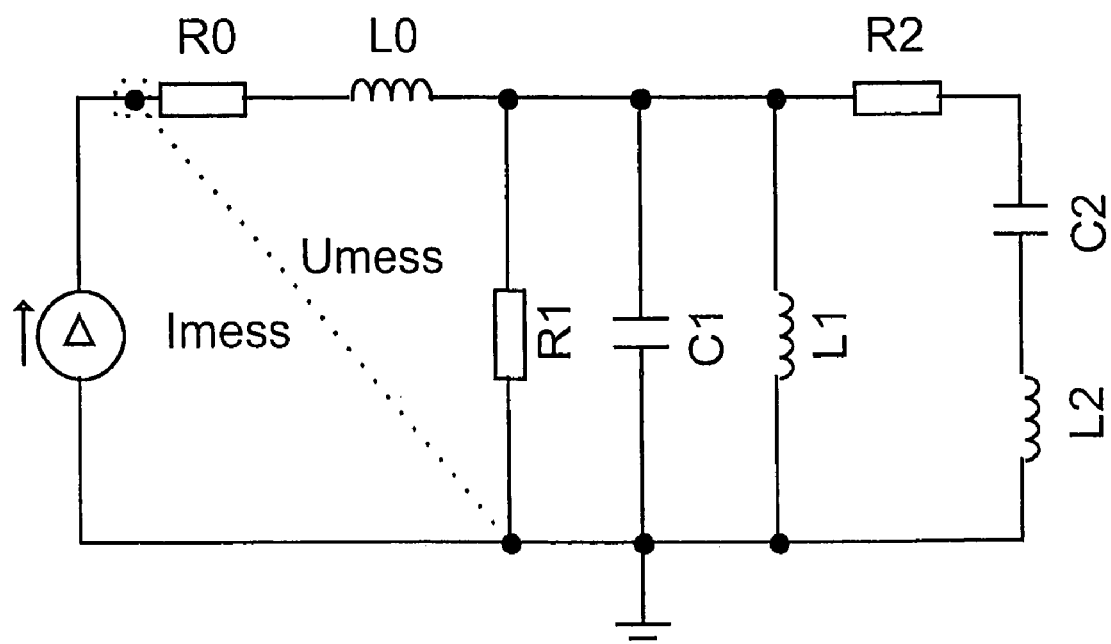

METHOD AND DEVICE FOR MEASURING OPERATIONAL DENSITY AND/OR OPERATIONAL SOUND VELOCITY IN A GASEOUS MEDIUM

CROSS-REFERENCE TO RELATED APPLICATIONS

This application claims priority under 35 USC 119 of German Application No. 10 2006 013 809.0 filed on Mar. 22, 2006.

BACKGROUND OF THE INVENTION

The invention relates to a method and a device for measuring operational density and/or operational sound velocity in a gaseous medium.

In the sector of gas measurement technology, one constantly encounters the same measurement tasks. A characteristic variable of natural gas, which is very important, is density. However, determination of density is not trivial. Previous measurement methods are either expensive or require a lot of space.

Such a measurement method is described in German Patent No. DE 37 41 558 A1, in which a device for determining the resonance frequency of a vibrating organ fundamentally in the form of a Helmholtz resonator is described. The density and the flow velocity of a fluid are determined from the resonance frequency. In this connection, the vibrating organ is fundamentally disposed in a housing, in the form of a Helmholtz resonator, and chambers having the same volume are provided on both sides of the vibrating organ, through which chambers the fluid flows. In this connection, the vibration of the vibrating organ is influenced by the fluid, and thereby changes the vibration behavior of the vibrating organ, in measurable manner, as a function of the density of the fluid. However, only a single frequency is measured as the resonance frequency, and the measurement device is optimized in targeted manner, to simplify the underlying interpretation of the measurement values. In the case of such an arrangement, no determination of the sound velocity is possible, either, since the determined single frequency does not yield this. Furthermore, this is a self-exciting vibration circuit, the resonance frequency of which can only be determined for an impedance maximum.

SUMMARY OF THE INVENTION

It is therefore the task of the present invention to further develop a method of the type stated and a device of the type stated, in such a manner that a more precise determination of the operational density is made possible, with the simultaneous possibility of determining the operational sound velocity.

The invention comprises a method for measuring operational density and/or operational sound velocity in a gaseous medium, using a sound transducer that is capable of vibrating, and is disposed in a housing in such a manner that chambers having the same volume are formed on both sides of the sound transducer, which are filled by the gaseous medium. The method provides that the chambers are connected with one another by way of an open channel having defined dimensions. The impedance of the sound transducer, which is influenced, in particular, by the density of the gaseous medium, is determined within a frequency range that can be established, using an exciter vibration applied to the sound transducer, as a function of the exciter frequency. From this, the operational density and/or the operational sound velocity of the gaseous medium are determined using a plurality of characteristic frequencies of the sound transducer vibrating in the gaseous medium.

This inventive method is based on the property of all gases of having not only a certain mass per volume, but also a surface-related resilience. Both variables are accessible by means of the measurement method presented here. In this way, the possibility exists to determine not only the operational density but also the operational sound velocity. In this connection, not only is a single resonance frequency determined, but rather, on the basis of the geometry of the chambers, the sound transducer, and the properties of the gaseous medium, an entire frequency spectrum is determined and examined for characteristic frequencies. Using theoretical derivations, the operational density and/or the operational sound velocity of the gaseous medium can be clearly determined, with a reasonable amount of calculation effort, from these characteristic frequencies and geometric variables that are stable over a long period of time, which depend on the configuration of the sound transducer and its surroundings, and can be reliably determined in advance. In this connection, the determination takes place essentially in real-time operation, since the vibration excitation and the vibration response of the sound transducer can be pre-determined and determined, respectively, essentially at the same time, in accordance with the superimposition principle.

Therefore, the values determined can be processed further very close in time, something that can be particularly advantageous in the case of time-critical regulation processes. In this connection, the sound transducer, the chambers having the same volume, and the open channel form approximately the arrangement of a Helmholtz resonator.

In contrast to known evaluation methods having a similar approach, a complete frequency range is evaluated in the case of the method according to the invention, and a plurality of characteristic frequencies is determined from the measurable progression of the impedance within the frequency range, which are representative for the operational density and the operational sound velocity of the gaseous medium, as can be shown analytically. It is therefore possible to determine both variables. In this connection, it is advantageous that the mechanical impedance of the vibrating, excited sound transducer, which is influenced by the density of the gaseous medium, is evaluated at the same time as an electrical impedance of the sound transducer.

In practice, it is advantageous to determine three characteristic frequencies for determining the impedance of the sound transducer, of which one of the characteristic frequencies of the sound transducer results from the geometry of the sound transducer, and other, advantageously two other characteristic frequencies result from the interaction between sound transducer and gaseous medium. In this connection, each characteristic frequency is determined from the measured progression of the impedance, in that it occurs at locations of the frequency response at which the imaginary part of the impedance becomes zero. In this way, a clear criterion that can be formulated in a mathematically simple manner is obtained for determining the characteristic frequencies, using the measured impedances.

It is advantageous if the impedance measurement is carried out by means of a current measurement and a voltage measurement on the sound transducer, which can be carried out at the same time, particularly in accordance with the superimposition principle. In the case of the current measurement, the current that changes over time is determined, which is applied to the sound transducer to excite the vibration. In this connection, the current that changes over time can be formed from a frequency spectrum consisting of a current having frequencies with the same amplitude and different phase relation, the ratio of effective value and peak value of which is maximal. In the case of the voltage measurement, the voltage that changes over time is determined, which can be detected as a reaction to the vibrations of the sound transducer influenced by the gaseous medium.

It is particularly advantageous that the evaluation of the current measurement and the voltage measurement can be carried out analytically. It is particularly advantageous if the evaluation of the current measurement and the voltage measurement is carried out using Fast Fourier Transformation. In this way, no particular numerical effort is required for the evaluation, but instead, the variable being sought, in each instance, can be directly determined from the transformed or back-transformed values, by means of suitable formulation. In this way, the calculation effort is clearly reduced.

It can be shown that the operational density $\rho_B$ can be calculated, in particularly advantageous manner, from $$\rho_B = \frac{S_K \cdot m_M}{S_M^2 \cdot l_K} \cdot \left(\frac{f_3^2}{f_2^2} - 1\right) \cdot \left(1 - \frac{f_1^2}{f_2^2}\right),$$

wherein:
$S_M$—surface size of the region of the sound transducer that is capable of vibrating,
$m_M$—mass of the region of the sound transducer that is capable of vibrating,
$S_K$—cross-sectional surface of the channel between the chambers,
$l_K$—length of the channel between the chambers, and
$f_1, f_2, f_3$—determined characteristic frequencies.

In this way, the operational density $\rho_B$ can be determined solely from variables of the sound transducer that are predetermined in fixed manner and remain essentially the same over time, as well as from the determined characteristic frequencies, so that the main effort of calculation can be seen in determining the characteristic frequencies. If applicable, additional correction factors are added to the factors that influence the operational density, which are derived, for example, from the geometry of the measurement element, as well as from other influence variables, and are required for calibration, for example.

Analogously, it holds true for the calculation of the operational sound velocity $c_B$ that the operational sound velocity $c_B$ is calculated from $$c_B = 2\pi \cdot f_2 \cdot \sqrt{\frac{V \cdot l_K}{2 \cdot S_K}}$$

wherein:
V—volume of the two chambers,
$S_K$—cross-sectional surface of the channel between the chambers,
$l_K$—length of the channel between the chambers, and
$f_2$—determined characteristic frequency.

Here again, only variables of the sound transducer that remain essentially the same over time, as well as one of the characteristic frequencies, are required. In this connection, operational density $\rho_B$ and operational sound velocity $c_B$ can be determined independent of one another. If applicable, here again additional correction factors are added to the factors that influence the operational sound velocity, which are derived, for example, from the geometry of the measurement element, as well as from other influence variables, and are required for calibration, for example.

It is furthermore advantageous if temperature and pressure of the gaseous medium within the chambers are determined during the impedance measurement. In this way, in a further embodiment, the standard densities and the standard sound velocity of the gaseous medium can be calculated from the temperature and the pressure of the gaseous medium within the chambers, using the status equation for ideal gases, from the determined operational density and the operational sound velocity. In this way, the values for operational density $\rho_B$ and operational sound velocity $c_B$ that were determined directly can be converted into the corresponding standard variables, without significant measurement effort having to be expended for this purpose.

It is advantageous if the determination of the impedance of the sound transducer is carried out in an evaluation unit to which the measurement values of current and voltage that change over time are applied by way of a digital/analog converter or analog/digital converter, respectively, in a further embodiment. In the evaluation unit, which can be particularly designed to carry out the corresponding calculation methods, all of the necessary calculations, evaluations, and protocols can therefore be carried out centrally.

The invention also relates to a device for measuring operational density and/or operational sound velocity in a gaseous medium, using a sound transducer that is capable of vibrating, which is disposed in a housing in such a manner that chambers having the same volume are formed on both sides of the sound transducer, which are filled by the gaseous medium so that the gaseous medium has the same volume in each chamber. The chambers are connected with one another by way of an open channel having defined dimensions. A defined exciter vibration can be applied to the sound transducer, and a measurement device detects the vibration response of the sound transducer, which is influenced, in particular, by the density of the gaseous medium, within a frequency range that can be established, and corresponds to the impedance of the sound transducer, as a function of the exciter frequency. From this, an evaluation unit calculates the operational density and/or the operational sound velocity of the gaseous medium, using a plurality of characteristic frequencies of the sound transducer vibrating in the gaseous medium.

It is advantageous in the embodiment of such a device if the chambers are configured of equal size and symmetrically, and furthermore the geometric dimensions of the chambers and/or of the open channel are configured in such a manner that similar conditions for gaseous medium and sound transducer form for both chambers. In this way, simple geometrical and physical conditions form in the chambers and for the interaction of the gaseous medium between the chambers and the sound transducer, which simplify a calculation of the characteristic frequencies and therefore of the operational density and/or operational sound velocity.

In a further embodiment, the open channel can be configured in the form of a pipe-shaped section that projects into the chambers on both sides of the sound transducer. The cross-section of the open channel should preferably be configured to be greater than one-tenth of the vibrating surface of the sound transducer, in order to reduce the mechanical losses. Likewise, the feed lines for the gaseous medium to the chambers having equal volume should have a great length in relation to their cross-section.

For the embodiment of the sound transducer, it is advantageous if the sound transducer is an electro-acoustical transducer, which can be configured as an electrostatic sound transducer, a piezoelectric sound transducer on a polymer basis, or also as an electrodynamic sound transducer.

BRIEF DESCRIPTION OF THE DRAWINGS

A particularly preferred embodiment of the device according to the invention as well as of the deliberations and conditions in the implementation of the method according to the invention are shown in the drawing.

This shows.

DETAILED DESCRIPTION OF THE PREFERRED EMBODIMENTS

Figure 1:
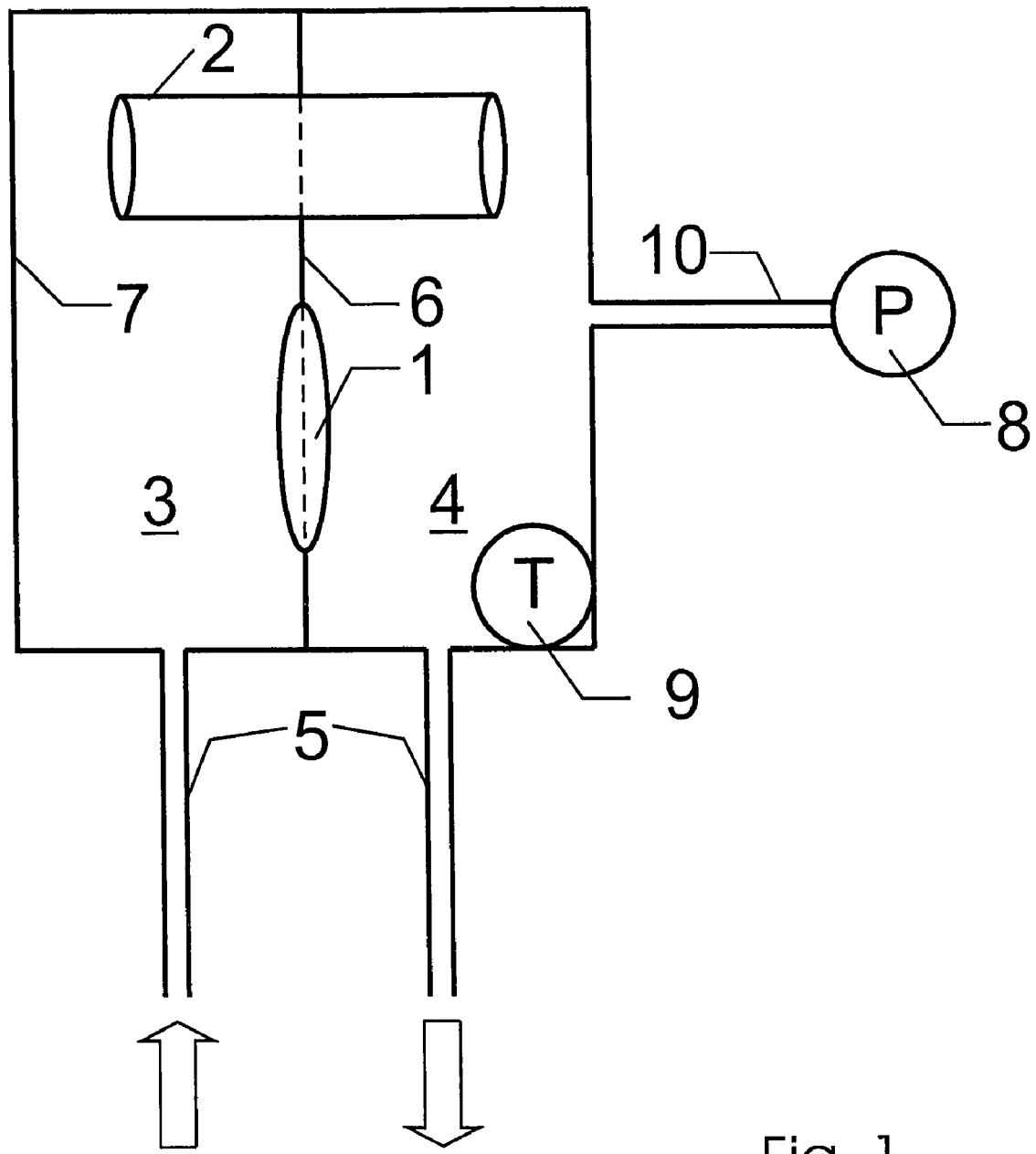
FIG. 1—fundamental structure of a measurement cell of the device according to the invention, FIG. 2—simplified equivalent circuit diagram, FIG. 3—expanded equivalent circuit diagram, FIG. 4—phase response of the system, with $L_0=0$ and $L_0=0.4$ mH, FIG. 5—phase responses of the system with $L_0$ calculated out when halving and doubling the operational density as compared with the normal state, assuming the sound velocities are the same, FIG. 6—phase responses at 0.71 times and 1.41 times the sound velocity, assuming the operational densities are the same, and FIG. 7—block schematic of the device components for determining the impedance.

In FIG. 1, the fundamental structure of a measurement cell of the device according to the invention is shown. In this connection, the measurement cell has a closed housing 7, which is divided into two chambers 3, 4 of equal size by a partition 6. An open channel 2 that is well defined in terms of its dimensions, as well as a sound transducer 1, are let into the partition 6. The gaseous medium to be measured enters and leaves the housing 7 through comparatively thin and long feed pipes 5. By measuring the electrical impedance of the sound transducer 1 above the frequency, not only the operational density but also the operational sound velocity can be derived, after correction and conversion that will be explained in detail below, as can the dynamic viscosity, if applicable (although this will not be explained in greater detail below). By additional determination of the operational pressure and the operational temperature by means of suitable measurement pick-ups 8, 9, whereby the pressure pick-up stands in connection with one of the chambers 3, 4 by way of a connecting line 10, standard density and standard sound velocity can be determined after calculation.

In the following, the fundamental physical relationships between measurement values and target values of the method will be derived and explained.

The sound transducer 1 possesses a membrane that is capable of vibrating, which has an effective membrane surface $S_M$. The membrane can either move in piston form, or can perform a bending vibration of the $1^{st}$ order. Independent of the movement mode of the membrane, the membrane is additionally described by its mass $m_M$ as well as the active resilience $c_M$. In this way, a system capable of vibrating, having the resonance frequency $f_0$, is obtained. The following holds true:

$$f_0 = \frac{1}{2\pi} \cdot \frac{1}{\sqrt{C_M m_M}} \tag{G1}$$

By means of the installation of the sound transducer 1 into the closed housing 7, the membrane is stressed by the two equally large volumes V of the housing chambers 3, 4. If one imagines the open channel 2 not to be present, the two volumes V act as additional resiliences $C_V$, which increase the resonance frequency of the membrane. The resiliences $C_V$ are calculated from the volume V, the membrane surface $S_M$, the operational pressure $P_B$, as well as the adiabatic coefficient $\kappa$, as:

$$C_V = \frac{V}{\kappa \cdot P_B} \cdot \frac{1}{S_M^2} \tag{G2}$$

Since the resiliences $C_V$ act on both sides of the membrane, the total load for the membrane is $C_V/2$.

Now the open channel 2 comes into play. It can be characterized by its length $l_K$ as well as its cross-section $S_K$. Together with the volumes V of the two housing chambers 3, 4, it also forms a system capable of vibrating, having the resonance frequency $f_2$, which can be calculated as follows, taking the operational sound velocity $c_B$ into consideration:

$$f_2 = \frac{c_B}{2\pi} \cdot \sqrt{\frac{2S_K}{V \cdot l_K}} \tag{G3}$$

The operational sound velocity can also be described by means of the operational density $\rho_B$, the operational pressure $P_B$, as well as the adiabatic coefficient $\kappa$, as:

$$c_B = \sqrt{\frac{\kappa \cdot P_B}{\rho_B}} \tag{G4}$$

Therefore the resonance frequency $f_2$ can also be expressed as follows:

$$f_2 = \frac{1}{2\pi} \cdot \sqrt{\frac{2S_K \cdot \kappa \cdot P_B}{V \cdot l_K \cdot \rho_B}} \tag{G5}$$

If one now considers the stress that acts on the membrane, this consists not only of the total volume resilience $C_V/2$, but rather of a mass $m_K$ that is additionally produced by the communication channel. It can be calculated from the resonance frequency $f_2$, because:

$$f_2 = \frac{1}{2\pi} \cdot \sqrt{\frac{2}{C_V \cdot m_K}} \tag{G6}$$

Inserting $C_V$ from (G2) and equating with (G5) yields:

$$\frac{\kappa \cdot P_B \cdot S_M^2}{V \cdot m_K} = \frac{S_K \cdot \kappa \cdot P_B}{V \cdot l_K \cdot \rho_B} \Rightarrow m_K = S_M^2 \cdot \frac{l_K \cdot \rho_B}{S_K} \quad \text{(G7)}$$

If one considers the sound transducer 1 to be ideal, it can be described with its transducer constant W, which converts the mechanically complex variables $v_M$ (membrane velocity) and $F_M$ (membrane force), which act on the membrane, into the electrically complex variables u (voltage) and i (current), and vice versa:

$$u = W \cdot v_M \text{ and } i = \frac{F_M}{W} \quad \text{(G8)}$$

With this, the electrical equivalent circuit diagram according to FIG. 2 allows itself to be presented:

In this connection,

C1 is the equivalent of the membrane mass,
L1 is the equivalent of the membrane resilience,
C2 is the equivalent of the medium mass in the communication channel,
L2 is the equivalent of the resilience of the medium in the volumes.

Proceeding from the equivalent circuit diagram, the complex electrical impedance Z turns out to be $$Z = \frac{j\omega L1 - j\omega^3 L1L2C2}{1 - \omega^2(L1C1 + L2C2 + L1C2) + \omega^4 L1C1L2C2} \quad \text{(G9)}$$

Z has three characteristic circuit frequencies, in which the imaginary part disappears. The squares of these circuit frequencies can be calculated as $$\omega_1^2 = \frac{1}{2} \cdot \left(\frac{1}{L1C1} + \frac{1}{L2C2} + \frac{1}{L2C1}\right) - \sqrt{\frac{1}{4} \cdot \left(\frac{1}{L1C1} + \frac{1}{L2C2} + \frac{1}{L2C1}\right)^2 - \frac{1}{L1C1L2C2}} \quad \text{(G10)}$$

$$\omega_2^2 = \frac{1}{L2C2} \quad \text{(G11)}$$

$$\omega_3^2 = \frac{1}{2} \cdot \left(\frac{1}{L1C1} + \frac{1}{L2C2} + \frac{1}{L2C1}\right) + \sqrt{\frac{1}{4} \cdot \left(\frac{1}{L1C1} + \frac{1}{L2C2} + \frac{1}{L2C1}\right)^2 - \frac{1}{L1C1L2C2}} \quad \text{(G12)}$$

From this it can be derived that:

$$\omega_1^2 \cdot \omega_3^2 = \frac{1}{L1C1L2C2} \Rightarrow \frac{1}{L1C1} = \frac{\omega_1^2 \cdot \omega_3^2}{\omega_2^2} \quad \text{(G13)}$$

$$\omega_1^2 + \omega_3^2 = \frac{1}{L1C1} + \frac{1}{L2C2} + \frac{1}{L2C1} \Rightarrow \frac{1}{L2C1} = \omega_1^2 + \omega_3^2 - \omega_2^2 - \frac{\omega_1^2 \cdot \omega_3^2}{\omega_2^2} \quad \text{(G14)}$$

The single variable that is precisely quantifiable and stable in the long term is the equivalent of the membrane mass, so that the other reactances must relate to C1, in order to arrive at an analytical solution:

$$L1 = \frac{1}{C1} \cdot \frac{\omega_2^2}{\omega_1^2 \cdot \omega_3^2} \quad \text{(G15)}$$

$$L2 = \frac{1}{C1} \cdot \frac{\omega_2^2}{\omega_1^2 \cdot \omega_2^2 + \omega_3^2 \cdot \omega_2^2 - \omega_2^4 - \omega_1^2 \cdot \omega_3^2} \quad \text{(G16)}$$

$$C2 = C1 \cdot \left(\frac{\omega_1^2}{\omega_2^2} + \frac{\omega_3^2}{\omega_2^2} - 1 - \frac{\omega_1^2 \cdot \omega_3^2}{\omega_2^4}\right) \quad \text{(G17)}$$

Thus all of the reactances can be derived from the three characteristic frequencies.

Now the variables calculated from (G15) to (G17) are converted to the mechanical variables that are of interest, and the circuit frequencies are replaced with frequencies:

$$C_M = \frac{1}{m_M} \cdot \frac{f_2^2}{f_1^2 \cdot f_3^2} \quad \text{(G18)}$$

$$C_v = \frac{2}{m_M} \cdot \frac{f_2^2}{f_1^2 \cdot f_2^2 + f_3^2 \cdot f_2^2 - f_2^4 - f_1^2 \cdot f_3^2} \quad \text{(G19)}$$

$$m_K = m_M \cdot \left(\frac{f_1^2}{f_2^2} + \frac{f_3^2}{f_2^2} - 1 - \frac{f_1^2 \cdot f_3^2}{f_2^4}\right) \quad \text{(G20)}$$

From (G20) and (G7), the operational density $\rho_B$ proves to be:

$$\rho_B = \frac{S_K \cdot m_M}{S_M^2 \cdot l_K} \cdot \left(\frac{f_1^2}{f_2^2} + \frac{f_3^2}{f_2^2} - 1 - \frac{f_1^2 \cdot f_3^2}{f_2^4}\right) = \quad \text{(G21)}$$

$$\frac{S_K \cdot m_M}{S_M^2 \cdot l_K} \cdot \left(\frac{f_3^2}{f_2^2} - 1\right) \cdot \left(1 - \frac{f_1^2}{f_2^2}\right)$$

The operational sound velocity $c_B$ follows from (G3):

$$c_B = 2\pi \cdot f_2 \cdot \sqrt{\frac{V \cdot l_K}{2 \cdot S_K}} \quad \text{(G22)}$$

Herein lies the advantage of the device and of the method: After measurement of the three characteristic frequencies $f_1$, $f_2$, and $f_3$, the operational density $\rho_B$ results from the known geometric variables $S_K$, $S_M$, and $l_K$, which are stable in the long term, as well as the membrane mass $m_M$ of the sound transducer. The operational sound velocity $c_B$ is also based on the geometric variables V, $l_K$, and $S_K$, which are stable in the long term.

A practical implementation of the theoretical relationships explained above can be carried out as follows, for example:

An advantageous experimental arrangement for carrying out the method consists, for example, of an electrodynamic loudspeaker having a diameter of 45 mm as a sound transducer. The idealized defaults must be supplemented with four additional characteristic variables, which the sound transducer and the housing bring with them. These are the vibration coil resistance $R_0$, the vibration coil inductance $L_0$, the mechanical loss resistance of the membrane clamp $R_1$ (here already transformed into the electrical branch), as well as the mechanical flow resistance $R_2$ in the open channel (also transformed). With a current source as the signal generator and a voltage measurement by way of the electrical connectors of the sound transducer, an expanded equivalent circuit diagram according to FIG. 3 is obtained:

By measuring the impedance of the loudspeaker without housing, as well as in a closed housing having a defined volume, the following concrete mechanical and electrical variables can be determined:

$R_0$=47 Ω, $R_1$=100 Ω, $f_0$=485 Hz, $C_M$=2.2E−4 m/N,
$m_M$=5.0E−4 kg, $C_1$=40 uF, $L_0$=0.4 mH, $L_1$=2.7 mH.

The design of the chamber volumes as well as of the open channel takes place in such a manner that under the expected operational conditions, $C_1$=$C_2$ and $L_1$=$L_2$. The cross-section of the open channel should be greater than one-tenth of the membrane surface, in order to keep the mechanical losses small ($R_2$ as small as possible).

Figure 4:
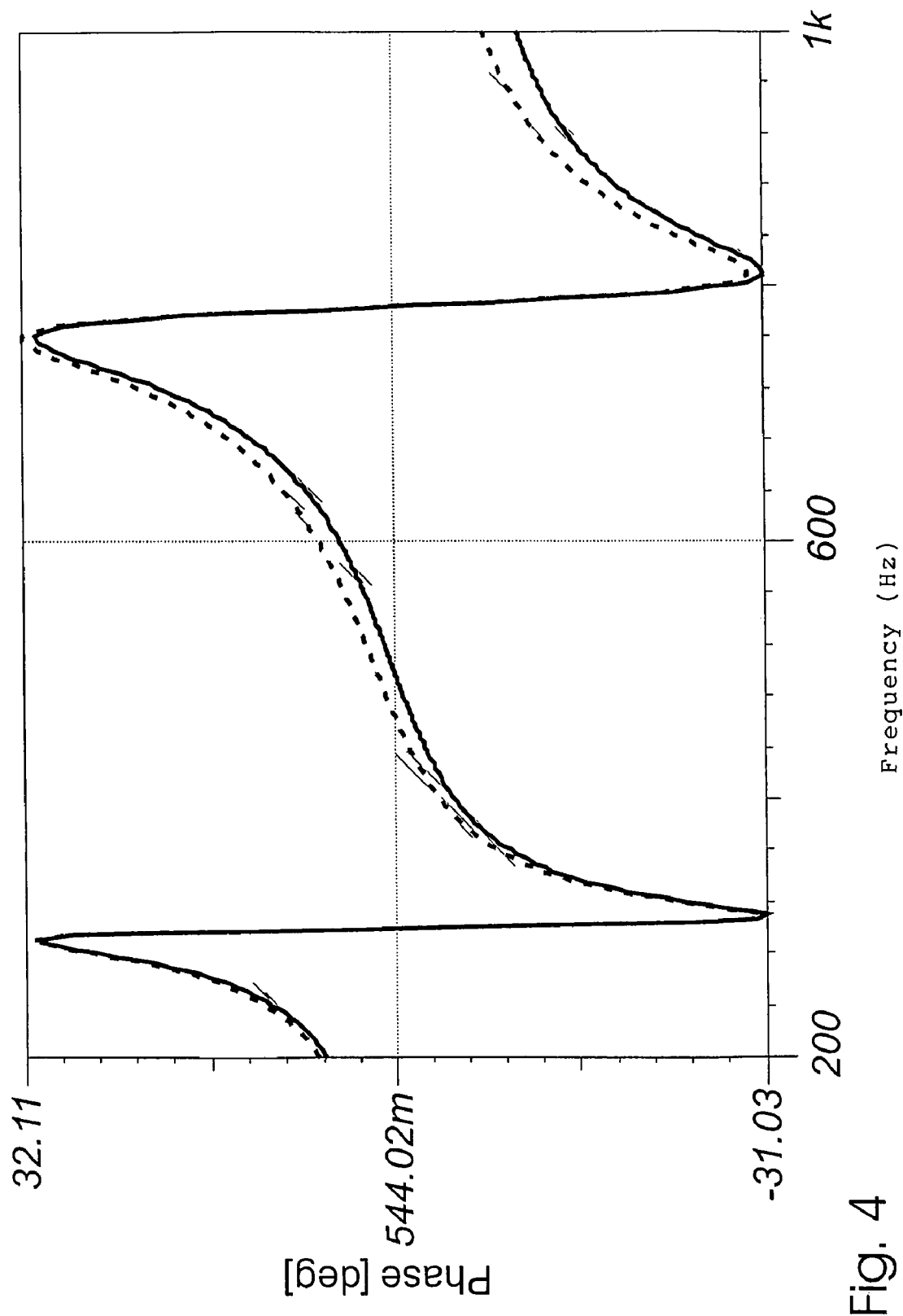

Since the three characteristic frequencies occur at locations at which the imaginary part of the impedance disappears, the critical influence variable proves to be the vibration coil impedance $L_0$. The diagram according to FIG. 4 shows the phase response of the system with $L_0$=0 and $L_0$=0.4 mH:

The different zero crossings of the phases at the frequency $f_2$ can be recognized: At $L_0$=0.4 mH, the zero crossing shifts towards a lesser frequency. Thus $L_0$ must be calculated out. The frequencies $f_1$ and $f_3$ are hardly affected.

Figure 5:
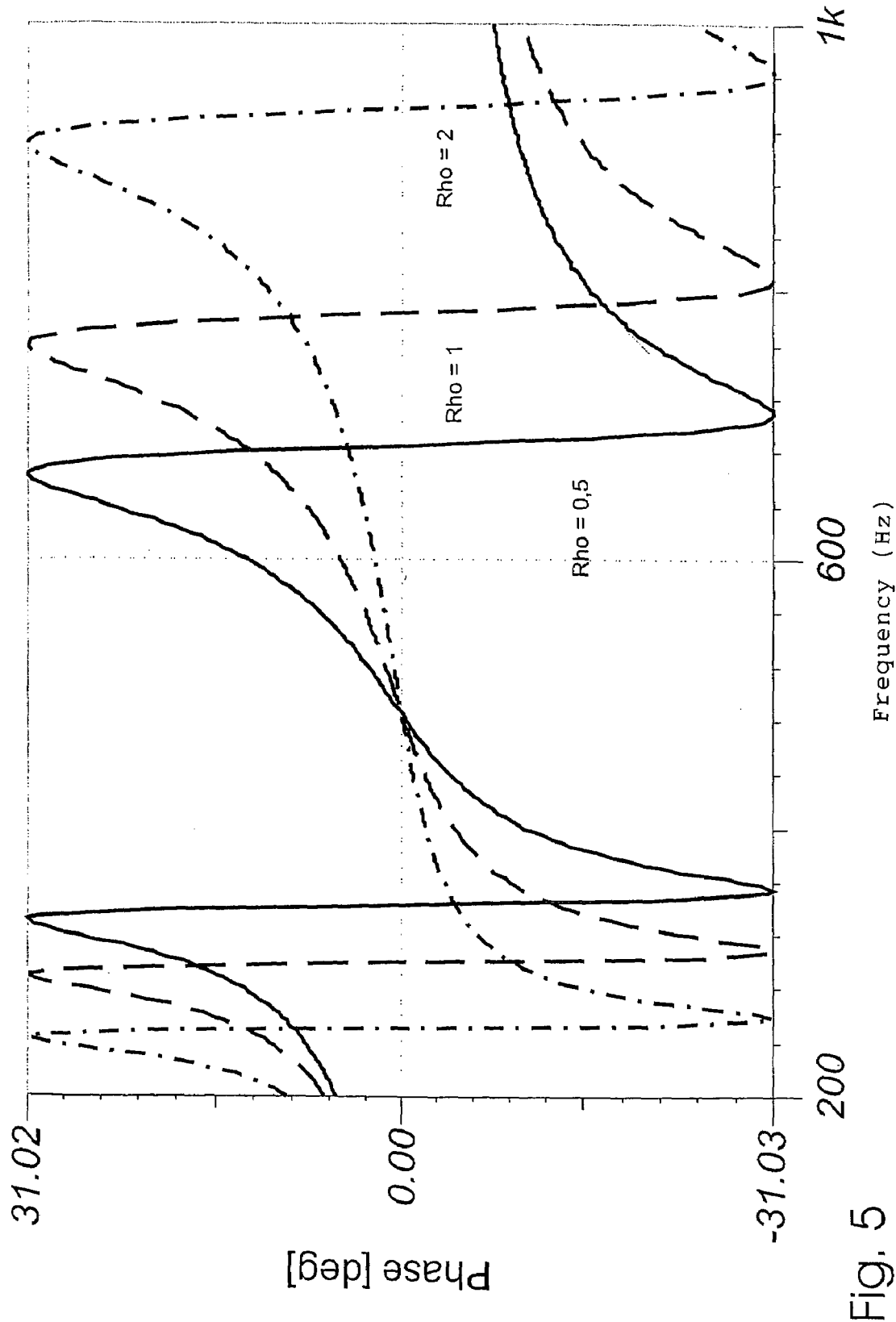

FIG. 5 shows the phase responses with $L_0$ calculated out when halving and doubling the operational density as compared with the normal state, assuming the same sound velocities.

Figure 6:
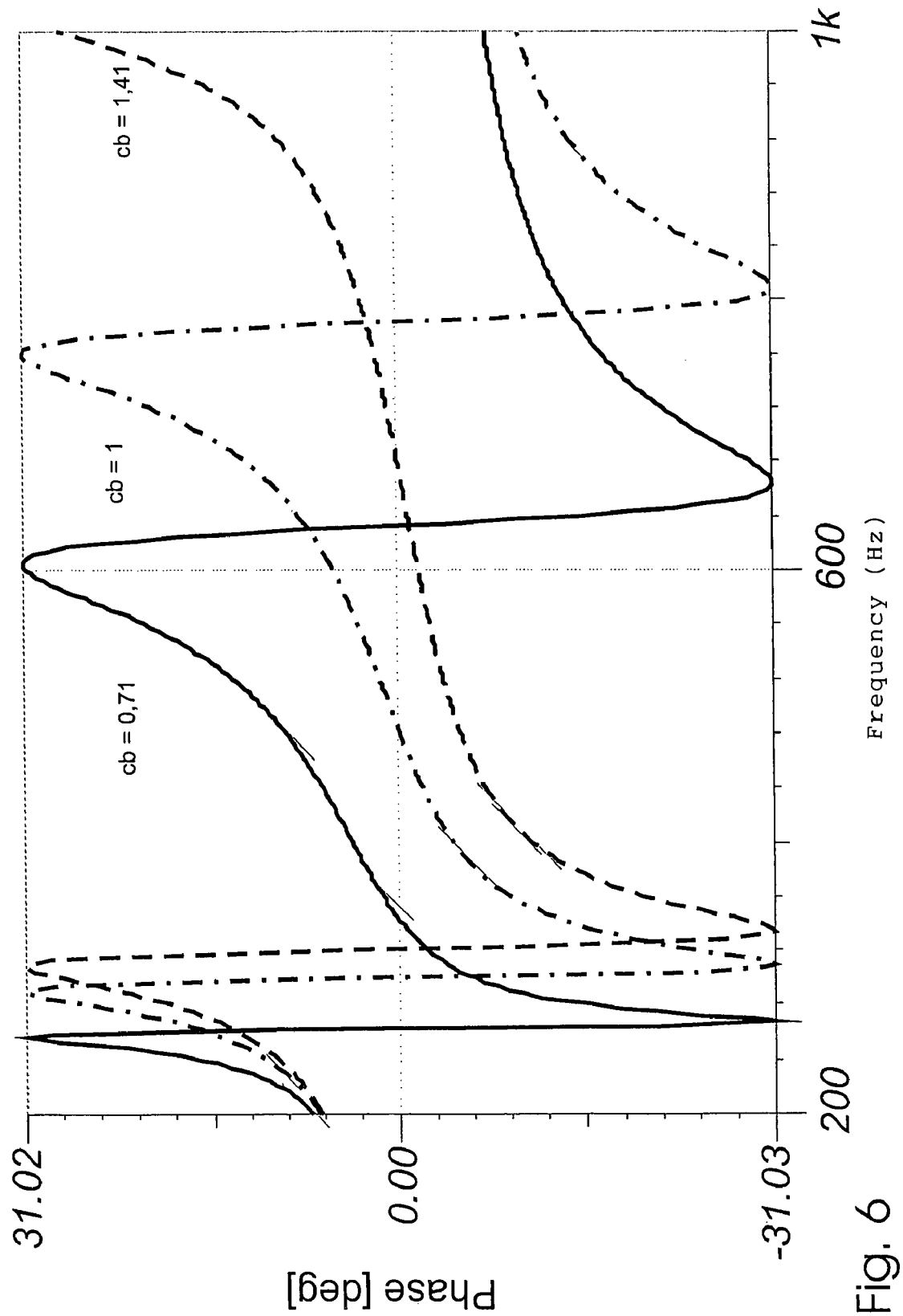

FIG. 6 shows the phase responses at 0,71 times and 1.41 times sound velocity, assuming the same operational densities.

Figure 7:
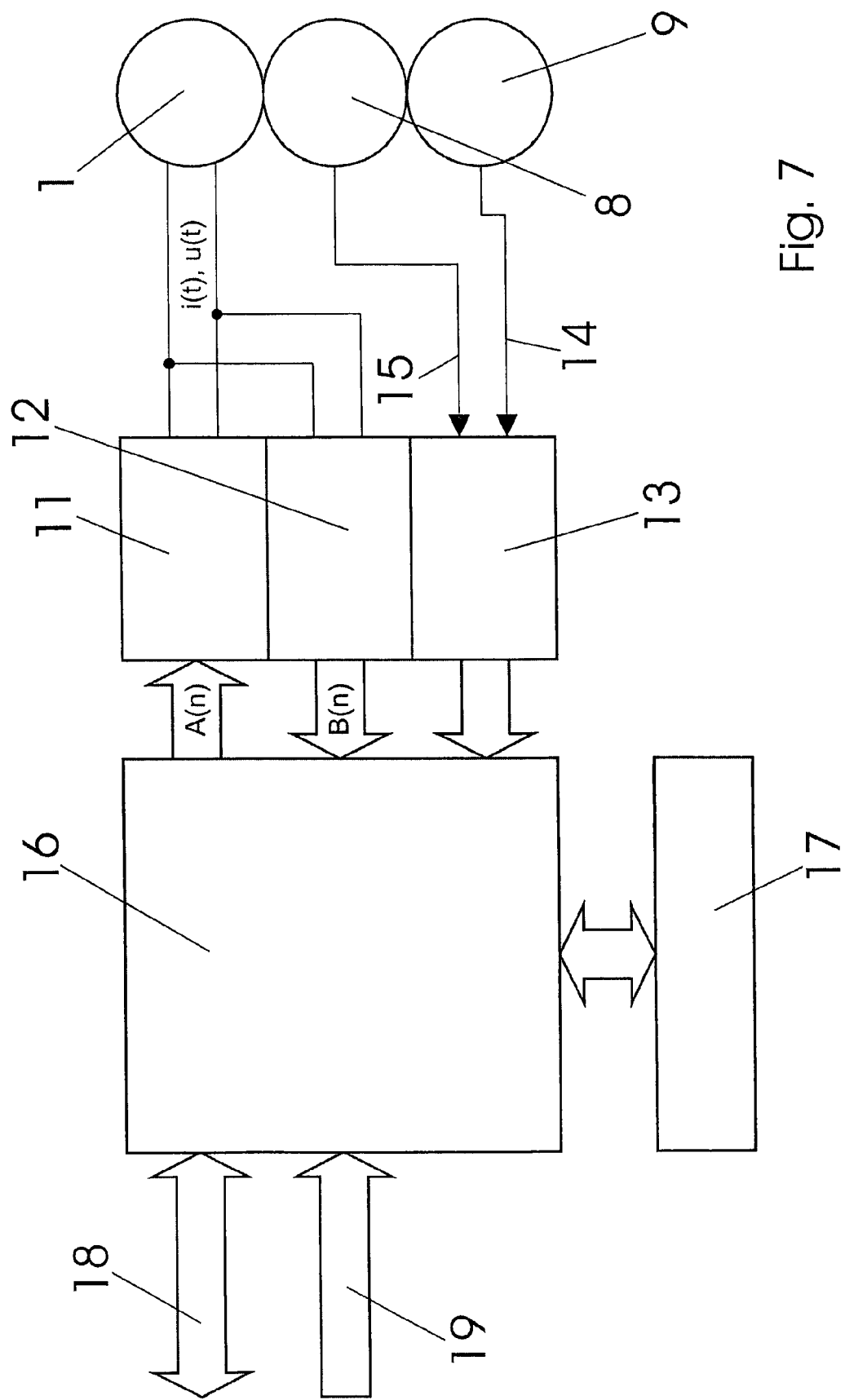

An advantageous method for measuring impedance could be carried out as follows, for example, according to FIG. 7:

The determination of the impedance of the sound transducer 1 takes place by way of an evaluation unit and by means of excitation of the sound transducer 1 with a well-defined current signal $i_{(t)}$, and determination of the voltage $u_{(t)}$ that occurs over the sound transducer 1. For this purpose, a block schematic is indicated in FIG. 7:

The current signal i(t) is generated by way of a digital/analog converter 11. For this purpose, an output sequence A consisting of N digital values is periodically passed to the D/A converter 11. The individual output digital values A(n) have the equidistant time interval $t_s$, so that the output sequence repeats after $t_p$. For the length N of the output sequence A, the following holds true:

$$N = \frac{t_p}{t_s} = 2^M \text{ with } M \text{ as a positive whole number} \tag{G23}$$

The individual output values A(n) of the output sequence A satisfy the calculation formula:

$$A(n) = A_0 \cdot \sum_{k=1}^{\frac{N}{2}-1} \cos\left(2 \cdot \pi \cdot \frac{k \cdot n - k^2}{N}\right) \text{ with } 0 \leq n \leq N-1 \tag{G24}$$

Shown in illustrative manner, the output sequence A(n) and therefore the current signal i(t) consist of a frequency spectrum formed from discrete frequencies having the same amplitude and optimally distributed different phase relation. The smallest frequency that occurs, identical with the distance of the discrete frequencies from one another, is $f_p$=1/$t_p$. The greatest frequency that occurs is $f_s$/2−$f_p$ with $f_s$=1/$t_s$. The different phase relation of the individual frequencies relative to one another is optimal in the sense that the ratio of effective value and peak value of the current signal is maximal.

Because of the composition of the current signal i(t) as indicated above, the use of a Fast Fourier Transformation (FFT) without windows for the N output values of the output sequence A offers loss-free representation of the complex frequency spectrum I(f).

Detection of the voltage u(t) that occurs over the sound transducer 1 takes place using an analog/digital converter 12. The time between scans amounts to $t_s$. N scanning values yield the input sequence B and thereby replicate u(t).

By means of using FFT on the input sequence B, the complex frequency spectrum U(f) is obtained. Thus the complex impedance of the sound transducer Z(f) can be determined by means of discrete complex division of U(f) by I(f).

Afterwards, subtraction of the impedance of $L_0$ and a search for the three characteristic frequencies $f_1$ to $f_3$ take place in the evaluation unit 16. These lie in those intervals in which a change in sign of the imaginary part has taken place. By means of interpolation into the surroundings of these intervals, the zero crossings can be precisely determined.

For the practical implementation explained above, a signal scanning rate $f_s$ of at least 3000 Hz is required. A sufficiently accurate resolution of the phase response presupposes a distance between the individual frequency lines of less than 2 Hz. As a result, M=11 and therefore N=2048. Thus, the sound velocity and the density can be measured approximately 1.5 times per second. The variation can be reduced by means of averaging over several measurements.

An expansion of the method can take place in that the values determined for operational density and operational sound velocity are converted to the standard values, as shown below.

By means of additional measurement of the operational pressure $P_B$ and the operational temperature $T_B$ by means of two pick-ups 8, 9, which are introduced into the chambers 3, 4, the standard density $\rho_n$ and the standard sound velocity $c_n$ can be calculated from the operational sound velocity $c_B$ and the operational density $\rho_B$, by means of the use of the status equation for ideal gases. In this connection, $P_n$ and $T_n$ establish the standard state. As long as $T_B$ and $T_n$ as well as $P_B$ and $P_n$ do not lie more than 20% apart from one another, the error due to the real gas behavior is less than 0.1%.

The following holds true:

$$\rho_n = \rho_B \cdot \frac{T_B \cdot P_n}{T_n \cdot P_B} \tag{G25}$$

$$c_n = c_B \cdot \sqrt{\frac{T_B}{T_n}} \tag{G26}$$

Data recording in the evaluation unit 16, of the electrical signals 14, 15 generated by the pressure and temperature pick-up 8, 9, takes place by means of A/D conversion in a dual converter module 13, and therefore the measurement values are available to the evaluation unit 16 in digital form.

For operation of the evaluation unit 16, an optional operating unit 17 is available, as is a power supply unit 19 for a connection to the power supply, and a communication unit 18 for passing on the values that have been determined.

| Reference Number List | |
|---|---|
| 1 | sound transducer |
| 2 | open channel |
| 3 | chamber |
| 4 | chamber |
| 5 | feed lines |
| 6 | partition |
| 7 | housing |
| 8 | pressure pick-up |
| 9 | temperature pick-up |
| 10 | connecting line, pressure pick-up |
| 11 | D/A converter |
| 12 | A/D converter |
| 13 | A/D converter |
| 14 | temperature signal |
| 15 | pressure signal |
| 16 | evaluation unit |
| 17 | operating unit |
| 18 | communication unit |
| 19 | power supply unit |

The invention claimed is:

1. A method for measuring at least one parameter selected from the group consisting of operational density and operational sound velocity in a gaseous medium, using a sound transducer that is capable of vibrating, and which is disposed in a housing so that chambers having the same volume and filled by the gaseous medium are formed on both sides of the sound transducer, the chambers being connected with one another by way of an open channel having defined dimensions, the method comprising the following steps:
applying an exciter vibration to the sound transducer;
determining impedance of the sound transducer, which is influenced by density of the gaseous medium, as a function of frequency, within an established frequency range; and
determining the at least one parameter of the gaseous medium using a plurality of characteristic frequencies of the sound transducer vibrating in the gaseous medium.

2. A method according to claim 1, wherein a mechanical impedance of the vibrating sound transducer, which is influenced by the density of the gaseous medium, is evaluated at the same time as an electrical impedance of the sound transducer.

3. A method according to claim 1, wherein one of the characteristic frequencies of the sound transducer is determined by geometry of the sound transducer, and other characteristic frequencies are determined by interaction between the sound transducer and gaseous medium.

4. A method according to claim 3, wherein three characteristic frequencies are determined for the determination of the impedance of the sound transducer.

5. A method according to claim 3, wherein the characteristic frequencies occur at locations of the frequency response at which an imaginary part of the impedance becomes zero.

6. A method according to claim 1, wherein the step of determining impedance is carried out by means of a current measurement and a voltage measurement on the sound transducer.

7. A method according to claim 6, wherein the current measurement and the voltage measurement are carried out at the same time, in accordance with a superimposition principle.

8. A method according to claim 6, wherein the current measurement detects current that can change over time, which is applied to the sound transducer for exciting the vibration.

9. A method according to claim 8, wherein the current, which can change over time, is formed from a frequency spectrum having frequencies of the same amplitude and different phase relation, whose ratio of effective value and peak value is maximal.

10. A method according to claim 6, wherein the voltage measurement detects voltage that can change over time, which can be detected as a reaction to the vibrations of the sound transducer influenced by the gaseous medium.

11. A method according to claim 6, wherein evaluation of the current measurement and of the voltage measurement is carried out analytically.

12. A method according to claim 11, wherein the evaluation of the current measurement and of the voltage measurement is carried out using Fast Fourier Transformation.

13. A method according to claim 1, wherein an operational density $r_B$ is calculated from $$\rho_B = \frac{S_K \cdot m_M}{S_M^2 \cdot l_K} \cdot \left(\frac{f_3^2}{f_2^2} - 1\right) \cdot \left(1 - \frac{f_1^2}{f_2^2}\right),$$

wherein:
$S_M$ is a surface size of a region of the sound transducer that is capable of vibrating,
$m_M$ is a mass of the region of the sound transducer that is capable of vibrating,
$S_K$ is a cross-sectional surface of the channel between the chambers,
$l_K$ is a length of the channel between the chambers, and
$f_1, f_2, f_3$ are determined characteristic frequencies.

14. A method according to claim 1, wherein an operational sound velocity $c_B$ is calculated from $$c_B = 2\pi \cdot f_2 \cdot \sqrt{\frac{V \cdot l_K}{2 \cdot S_K}}$$

wherein
V is a volume of the two chambers,
$S_K$ is a cross-sectional surface of the channel between the chambers,
$l_K$ is a length of the channel between the chambers, and
$f_2$ is the determined characteristic frequency.

15. A method according to claim 1, further comprising the step of measuring temperature and pressure of the gaseous medium within the chambers.

16. A method according to claim 15, wherein standard densities and a standard sound velocity of the gaseous medium are calculated from the temperature and the pressure of the gaseous medium within the chambers, using a status equation for ideal gases, from the determined operational density and the operational sound velocity.

17. A method according to claim 1, wherein the step of determining the impedance of the sound transducer is carried out in an evaluation unit.

18. A method according to claim 17, wherein measurement values of current and voltage of the sound transducer, which can change over time, are transmitted to the evaluation unit by way of a digital/analog converter or analog/digital converter.

19. A method according to claim 1, wherein the sound transducer works as an electro-acoustical transducer.

20. A method according to claim 1, wherein a dynamic viscosity of the gaseous medium is determined.

21. A method according to claim 1, wherein sound-transducer-specific variables are included in the calculation of the impedance.

22. A device for measuring at least one parameter selected from the group consisting of operational density and operational sound velocity in a gaseous medium, comprising:
- a housing;
- a sound transducer that is capable of vibrating, and which is disposed in said housing so that chambers having the same volume are formed on both sides of the sound transducer, said chambers being filled by the gaseous medium, wherein the gaseous medium in the chambers has the same volume on both sides of the sound transducer and the chambers are connected with one another by way of an open channel having defined dimensions, and a defined excitation vibration can be applied to the sound transducer;
- a measurement device that detects a vibration response of the sound transducer, said transducer being influenced by a density of the gaseous medium surrounding the sound transducer, within a frequency range that can be established, and corresponds to impedance of the sound transducer as a function of the frequency; and
- an evaluation unit that calculates the at least one parameter of the gaseous medium, using a plurality of characteristic frequencies of the sound transducer vibrating in the gaseous medium.

23. A device according to claim 22, wherein the chambers are configured to be of equal size and symmetrical.

24. A device according to claim 22, wherein geometrical dimensions of the chambers or of the open channel are configured so that similar conditions for gaseous medium and sound transducer exist in each chamber.

25. A device according to claim 22, wherein the open channel is configured in the form of a pipe-shaped section that projects into the chambers on both sides of the sound transducer.

26. A device according to claim 22, wherein feed lines for the gaseous medium to the chambers have a length that is substantially greater relative to their cross-section.

27. A device according to claim 22, wherein the sound transducer is an electro-acoustical transducer.

28. A device according to claim 27, wherein the sound transducer is an electrostatic sound transducer.

29. A device according to claim 27, wherein the sound transducer is a piezoelectric sound transducer on a polymer basis.

30. A device according to claim 27, wherein the sound transducer is an electrodynamic sound transducer.

31. A device according to claim 22, further comprising converter modules that convert analog measurement variables detected at the sound transducer to digitalized form for transmission to the evaluation unit, in order to determine the impedance in the evaluation unit.

32. A device according to claim 31, wherein the conversion of the measurement variables in the converter modules is carried out at a scanning rate of at least 3000 Hz.

33. A device according to claim 22, wherein the evaluation unit is configured for real-time implementation of Fast Fourier Transformations.

34. A device according to claim 22, wherein the evaluation unit is adapted to receive measurement values regarding temperature and pressure in the chambers.

35. A device according to claim 22, wherein a cross-section of the channel is configured to be greater than one-tenth of the vibrating surface of the sound transducer, in order to reduce mechanical losses.

* * * * *